US00PP27022P3

(12) United States Plant Patent
Olesen

(10) Patent No.: US PP27,022 P3
(45) Date of Patent: Aug. 9, 2016

(54) ROSE PLANT NAMED 'POULCAS041'

(50) Latin Name: ***Rosa* hybrid**
Varietal Denomination: Poulcas041

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 21 days.

(21) Appl. No.: 14/121,267

(22) Filed: Aug. 15, 2014

(65) Prior Publication Data

US 2016/0050808 P1 Feb. 18, 2016

(51) Int. Cl.
*A01H 5/02* (2006.01)

(52) U.S. Cl.
USPC ..... Plt./104

(58) Field of Classification Search
USPC ..... Plt./104
CPC ..... A01H 5/0222; A01H 5/0216
See application file for complete search history.

(56) References Cited

PUBLICATIONS http://poulsenroser.dk/media/73065/CASTLE-2013_LR_Poulsen-Roser.pdf; 2012; 2 pages.*

* cited by examiner

*Primary Examiner* — Kent L Bell

(57) ABSTRACT

A new garden rose plant which has abundant, yellow flowers and attractive foliage. This new and distinct variety has shown to be uniform and stable in the resulting generations from asexual propagation.

2 Drawing Sheets

Botanical designation: *Rosa* hybrid.
Variety denomination: 'Poulcas041'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2003 and the resulting seeds were planted in a controlled environment in Fredensborg, Denmark. The new variety, named 'Poulcas041', originated as a single seedling from the stated cross.

The new variety may be distinguished from its male pollen parent and female seed parent by the following characteristics. The female seed parent is 60 to 70 cm in height while the new plant is about 40 cm in height. The male pollen parent has flowers which are a red and yellow blend, while the new plant has yellow flowers.

The objective of the hybridization of this rose variety was to create a new and distinct variety for garden use with unique qualities, such as:

1. Uniform and abundant yellow flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulcas041' from all other varieties of which we are aware.

As part of the rose development program, Mogens N. Olesen germinated the seeds from the aforementioned hybridization during winter of 2003 and conducted evaluations on the resulting seedlings in a controlled environment in Fredensborg, Denmark. 'Poulcas041' was selected in the spring of 2004 by the inventor as a single plant from the progeny of the aforementioned hybridization.

Asexual reproduction of 'Poulcas041' by traditional budding and rooted cuttings was first done by Mogens N. Olesen in the nursery in Fredensborg, Denmark in July, 2004. This initial and other subsequent asexual propagations conducted in controlled environments have demonstrated that the characteristics of 'Poulcas041' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcas041'.

Specifically illustrated in FIG. 1 are open flowers, petals detached, flower buds, and reproductive flower parts.

DETAILED DESCRIPTION OF THE VARIETY

Figure 1:
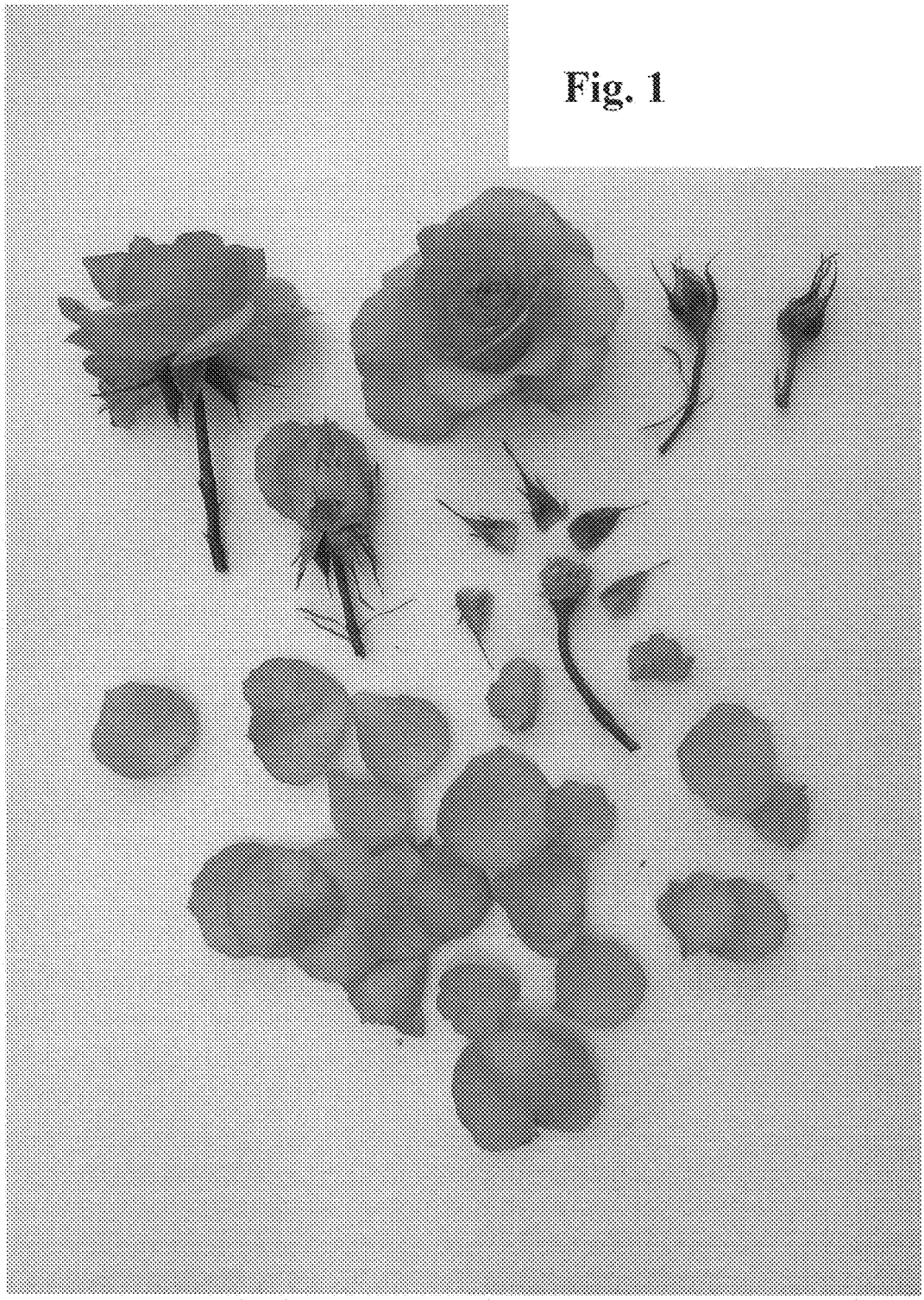
Figure 2:
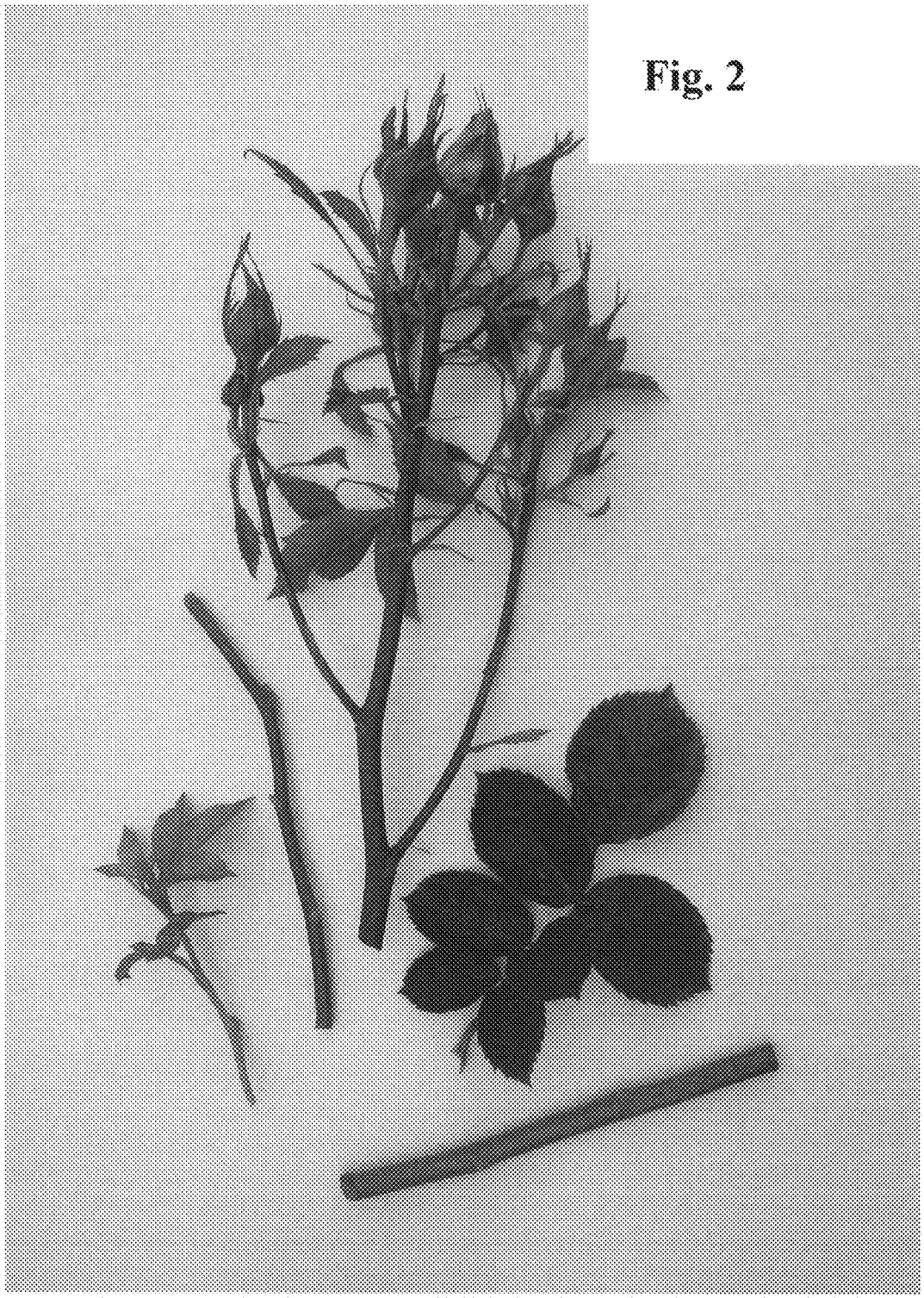
FIG. 2 shows a flowering branch, flower buds, leaves, and stems. Plants shown are 2 years of age.

The following is a description of 'Poulcas041', as observed in its growth in a field nursery in Marion County, Oreg. Observed plants are 2 years of age, and were grown on their own roots. Observed plants are 3 years of age, and were grown on *Rosa multiflora* understock. Color references are made using The Royal Horticultural Society (London, England) Colour Chart, 2001, except where common terms of color are used.

For a comparison, several physical characteristics of the rose variety 'Poulreb', U.S. Plant Pat. No. 12,534 dated Apr. 9, 2002, are compared to 'Poulcas041' in Chart 1.

CHART 1

| | 'Poulcas041' | 'Poulreb' |
|---|---|---|
| Petal Count | 35 petals | 60-75 petals |
| Flower Diameter | 80 mm | 70-80 mm |
| General Tonality of Flower Color | Yellow-Orange Group 16A | Yellow Group 8B |

FLOWER AND FLOWER BUD

Blooming habit: Continuous.

Flower bud:

*Size*.—Upon opening, 30 mm in length from base of receptacle to end of bud. Bud diameter is 18 mm.

*Bud form*.—Ovoid.

*Bud color*.—As sepals divide petals are Yellow-Orange Group 22A and Yellow Group 12C.

*Sepal inner surface*.—Color: Green Group 143D. Surface: Lightly pubescent.

*Sepal outer surface*.—Color: Yellow-Green Group 144A. Texture: Smooth.

*Sepal shape*.—Apex: Cirrhose. Base: Flat at union with receptacle.

*Sepal margin*.—Margins have moderate foliaceous appendages on three of the five sepals.

*Sepal size*.—35 mm long, 10 mm wide.

*Receptacle*.—Texture: Smooth. Size: 10 mm in height, 8 mm wide. Color: Yellow-Green Group 144A. Shape: Campanulate.

*Pedicel*.—Surface: Smooth. Length: 25 mm. Diameter: 3 mm on average. Color: Yellow-Green Group 144A. Strength: Strong.

*Peduncle*.—Length: 4 to 10 cm. Diameter: 4 mm. Color: Yellow-Green Group 144A. Occasionally, anthocyanin the color of Greyed-Purple Group 184A. Texture: Smooth.

Flower bud development: Flower buds are borne in clusters of 5 to 7 flower buds per stem.

Flower bloom:

*Fragrance*.—Weak floral scent.

*Duration*.—The blooms have a duration on the plant of approximately 10 days. Petals fall cleanly away from plant after flowers have fully matured.

*Size*.—Flower diameter is 80 mm when open. Flower depth is 30 mm.

*Flower shape*.—Rosette double flower with many slightly overlapping petals of different sizes.

*Shape of flower, side view*.—The upper portion is rounded. The lower portion is concave.

Petalage: Under normal conditions, flowers have 35 petals total, 5 of which are petaloids.

General tonality of flower: Open flowers are Yellow-Orange Group 16A.

Petal color:

*Upon opening, outer petals*.—Upper surface: Yellow Group 13B. Lower surface: Yellow-Orange Group 22C at the middle and marginal zone. At the base of the petal Yellow Group 12A.

*Upon opening, inner petals*.—Upper surface: Yellow Group 13B. Lower surface: Orange Group 24B at the marginal zone, blending with Yellow Group 12A at the middle zone. The base of the petal is Yellow Group 12A.

*After opening, outer petals*.—Upper surface: Yellow Group 13B. Lower surface: Yellow-Orange Group 22C at the middle and marginal zone. At the base of the petal Yellow Group 12A.

*After opening, inner petals*.—Upper surface: Yellow Group 13B. Lower surface: Yellow-Orange Group 22C at the middle and marginal zone. At the base of the petal Yellow Group 12A.

Petals:

*Petal reflex*.—Strong.

*Margin*.—Entire and uniform. Weak undulations. Slight point at the apex.

*Shape*.—Generally rounded. Apex shape: Rounded. Base shape: Rounded.

*Size*.—35 mm (l)×35 mm (w).

*Texture*.—Smooth.

*Thickness*.—Average.

Petaloids:

*Size*.—20 mm (l) by 20 mm (w).

*Quantity*.—5 on average.

*Shape*.—Elliptical. Apex and base are acute.

*Margins*.—Strong undulations.

*Color*.—Upper surface is Yellow Group 12A. Undersurface is Yellow-Orange Group 22B.

Reproductive organs:

*Pollen*.—None observed.

*Anthers*.—Size: 2 mm in length. Color: Yellow Group 12B. Quantity: 55 on average.

*Filaments*.—Color: Yellow-Orange Group 15A. Length: 6 mm.

*Pistils*.—Length: 5 mm. Quantity: 30 on average.

*Stigmas*.—Color: Greyed-Yellow Group 160A.

*Styles*.—Color: Green-White Group 157A with intonations of Red Group 51A.

*Location of stigmas*.—Level in location relative to the length of the filaments and the height of the anthers.

*Hips*.—None Observed.

PLANT

Plant growth: Upright, compact, bushy. Plants are 40 to 45 cm in height, and 40 cm wide.

Stems:

*Color*.—Juvenile growth: Yellow-Green Group 145A. Mature growth: Yellow-Green Group 146C.

*Length*.—On average, canes are 20 cm from the base of the plant to the flowering portion.

*Diameter*.—5 mm.

*Internodes*.—On mature canes, 30 to 50 mm between nodes.

*Surface texture*.—Young wood: Smooth. Older wood: Smooth.

Long prickles:

*Incidence*.—12 prickles per 10 cm of stem.

*Size*.—Average length of prickles on mature stems is 11 mm.

*Shape*.—Upper portion is linear. Lower portion is concave.

*Color*.—Juvenile prickles: Greyed-Yellow Group 160B. Mature prickles: Greyed-Purple Group 184B.

Plant foliage:

*Compound leaf.*—115 mm (l)×85 (w).

*Quantity.*—3 leaves per 10 cm of stem on average.

*Leaf bearing angle to the stem.*—45 degrees.

*Color of juvenile foliage.*—Upper side: Yellow-Green Group 144B with marginal intonations the color of Greyed-Orange Group 173A. Lower side: Yellow-Green Group 144B with marginal intonations the color of Greyed-Orange Group 173A.

*Color of mature foliage.*—Upper side: Yellow-Green Group 147A. Lower side: Yellow-Green Group 147B.

Plant leaves and leaflets:

*Stipules.*—Size: 16 mm long, 3 mm wide. Quantity: 2 per compound leaf. Shape: Linear, slightly broad based with outward extending apices. Margins: Finely serrated. Color: Yellow-Green Group 146B.

*Petiole.*—Length: 16 mm. Diameter: 2 mm.

*Upper surface.*—Color: Yellow-Green Group 146A.

*Lower surface.*—Color: Yellow-Green Group 144A.

*Rachis.*—Length: 43 mm. Upper surface: Color: Yellow-Green Group 146A.

*Lower surface.*—Color: Yellow-Green Group 144A. Observations: Small prickles.

*Leaflet.*—Quantity: Normally 7 leaflets. Margins: Serrated. Size: On average terminal leaflets are 50 mm long, 35 mm wide. Shape: Generally elliptical. Base: Rounded. Apex: Cuspidate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa,* downy mildew *Peronospora sparsa,* rust *Phragmidium sps.,* black spot *Diplocarpon rosae,* and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

We claim:

1. A new and distinct variety of rose plant named 'Poulcas041', substantially as illustrated and described herein, due to its abundant yellow flowers, disease resistance, and extended period of bloom.

* * * * *